United States Patent [19]
Lotito et al.

[11] Patent Number: 5,731,998
[45] Date of Patent: Mar. 24, 1998

[54] METHOD AND APPARATUS FOR COMPARING A SAMPLE WITH A REFERENCE USING A SPIDER DIAGRAM

[75] Inventors: Christian Lotito, Claix; Mathieu Antoine, Villard-Bonnot; Guillermo Mayobre, La Combe de Lancey, all of France

[73] Assignee: Hewlett-Packard Company, Palo Alto, Calif.

[21] Appl. No.: 674,052

[22] Filed: Jul. 1, 1996

[30] Foreign Application Priority Data

Jul. 14, 1995 [EP] European Pat. Off. ............ 95111026

[51] Int. Cl.$^6$ ........................................ B41M 3/02
[52] U.S. Cl. ........................... 364/570; 395/140
[58] Field of Search ............... 364/570, 715.06, 364/715.07, 551.01; 395/140, 100

[56] References Cited

U.S. PATENT DOCUMENTS

| | | |
|---|---|---|
| 3,811,040 | 5/1974 | Weinfurt et al. |
| 4,527,240 | 7/1985 | Kvitash. |
| 4,930,519 | 6/1990 | Anderson et al. |
| 5,276,789 | 1/1994 | Besaw et al. ............ 395/140 |
| 5,511,158 | 4/1996 | Sims ....................... 395/140 |
| 5,557,547 | 9/1996 | Phaal ..................... 365/551.01 |

FOREIGN PATENT DOCUMENTS

0598484A2 12/1993 European Pat. Off.

*Primary Examiner*—Ellis B. Ramirez
*Assistant Examiner*—Thomas Peeso

[57] ABSTRACT

A spider-diagram type of display is used to compare measured parameter values of a sample of interest with reference values for the parameters. The reference values are derived from measurements on a specified reference set of samples selected from a group of samples for which parameter measurements are available. The derived reference values are represented in the spider diagram by predetermined reference values that together delimit, for example, a circle. The measured parameter values of the sample of interest are scaled before display according to a respective scaling factor determined for each parameter by the ratio of the predetermined and derived reference values for the parameter concerned.

13 Claims, 3 Drawing Sheets

METHOD AND APPARATUS FOR COMPARING A SAMPLE WITH A REFERENCE USING A SPIDER DIAGRAM

FIELD OF THE INVENTION

The present invention relates to a method and apparatus for comparing a sample with a reference using a spider diagram. By "spider diagram" is meant a display arrangement in which each of a plurality of sample parameters subject to measurement is represented along a respective one of a corresponding plurality of axes, these axes extending radially from a common point in angularly spaced relation; such diagrams are also known as "kiviat" diagrams.

In the present specification, the term "sample" is intended to be read in a broad sense to cover any element, entity, system or process which is capable of being measured such as, for example, a mechanical component, the human body, a computer network, a manufacturing process or, as in the specific example to be described below, a block of computer code.

BACKGROUND OF THE INVENTION

It is well known to use spider diagrams for representing the measured values of a plurality of parameters of a sample. Thus, in U.S. Pat. No. 4,527,240 (Kvitash) a spider diagram is used to display the values of a number of key parameters of a blood sample. More particularly, for a current sample, the measured value of each parameter is scaled according to the known global maximum and minimum for that parameter and the scaled value is next plotted along the corresponding spider-diagram axis. The plotted values are then joined up to form a pattern characteristic of the current sample. This current-sample pattern is then compared with a reference that has been similarly scaled; the reference may be either an annulus built from the range of normal values for each measured parameter or the set of mean values of such parameters.

One difficulty with the arrangement described in U.S. Pat. No. 4,527,240 is that the reference against which the current-sample pattern is compared is extremely irregular in shape which makes it harder to identify anomolies.

Furthermore, it may be noted that in the arrangement of U.S. Pat. No. 4,527,240 the reference values are predetermined, having been previously globally derived to give a good representation of the population as a whole. There is no mechanism provided by which the current sample can be compared with a reference based on a specified set of one or more previously measured samples.

EP 0,598,484 (Hewlett-Packard Company) also describes a system utilising spider diagrams to display the measured values of a plurality of sample parameters; in this case, the sample under consideration is a communications network. In EP 0,598,484, for each parameter two alarm thresholds are specified (for example, a "warning" and a "danger" threshold). The scaling along each parameter axis is then independently adjusted such that the two corresponding thresholds have values of 1 and 2 respectively. As a result, the warning thresholds for all parameters form a circle of radius 1 whilst the danger thresholds form a circle of radius 2. These threshold circles may be considered as references against which the current-sample measurements are compared.

Whilst the provision of threshold circles in EP 0,598,484 makes the spotting of anomolies easier as compared with the reference-pattern arrangement of U.S. Pat. No. 4,527,240, EP 0,598,484 also relies on the presetting of the reference (threshold) values—though in EP 0,0,598,484 it is possible for the operator to adjust these values. Thus, again, there is no mechanism provided by which the current sample can be readily compared with a reference based on a specified set of one or more previously measured samples.

It is an object of the present invention to provide a method and apparatus for comparing, using a spider diagram, a current sample with a reference based on a specified set of one or more previously measured samples.

SUMMARY OF THE INVENTION

According to one aspect of the present invention, there is provided apparatus for comparing measured values of a plurality of parameters of a current sample of interest with reference values for said parameters, the apparatus comprising:

- a data store for storing measurements of said parameters for each sample of a group of samples;
- selection means enabling user selection from said group of a reference set of at least one sample;
- processing means comprising:
    - first means for processing said measurements to derive therefrom respective reference values for the parameters;
    - second means for determining for each parameter a respective scaling factor corresponding to that adapted to transform the reference value for that parameter into a predetermined reference-point value, and
    - third means for taking the measured value of each parameter of the current sample, and appling thereto the scaling factor determined for that parameter whereby to produce a corresponding scaled measured value; and
- display means for displaying for each parameter along a respective one of a plurality of axes, the predetermined reference-point value and the scaled measured value determined for that parameter, said plurality of axes extending radially from a common point in angularly spaced relation.

The present invention offers much greater flexibility than the above-desribed prior art systems as now the reference against which the current-sample is compared can be readily derived to be appropriate to the domain concerned by storing generally appropriate sample data in the data store and thereafter making a finer selection specific to the current sample under scrutiny.

Preferably, the predetermined reference-point values are such that when displayed they lie on a circle (or possibly an ellipse), this circle (or ellipse) being also displayed as a reference. The displayed scaled measured values may also be joined together to form a polygon in order to facilitate comparison with the reference pattern. The parameter axes may be displayed in full, in part or even omitted entirely.

Although the reference may comprise only one sample to which the current sample is to be compared, generally the reference set will comprise a number of samples including the current sample itself. In this way, the current sample can be compared against its peers. Preferably, means are provided enabling user selection of any desired one of the samples of the reference set as the current sample. In addition, means may be provided for stepping through said set to take each sample in turn as said current sample.

In the case where the reference set comprises a plurality of samples, the aforesaid first means of the processing means is preferably arranged to derive the reference value of each parameter in terms of a mean of the measurements for that parameter associated with the samples in the reference set. Advantageously, the processing means further comprises means for determining for each parameter the corresponding maximum and minimum measurements for the samples in the reference set, the display means displaying these maximum and minimum values along the corresponding axis. In this latter case, the parameter axes are preferably not displayed except between said maximum and minimum values.

According to another aspect of the present invention, there is provided a method of comparing measured values of a plurality of parameters of a current sample of interest with reference values for said parameters, the method comprising the steps of:

- providing measurements of said parameters for each sample of a group of samples;
- selecting from said group a reference set of a plurality of said samples;
- processing said measurements to derive for each parameter a reference value corresponding to a mean of the measurements for that parameters for the samples in the reference set;
- providing a display including a reference circle of unit radius from the centre of which extend, at least notionally, a plurality of angularly spaced axes, each axis corresponding to a said parameter and the intersection of that axis with the reference circle defining a reference point representing said reference value for that parameter;
- determining a scaling factor for each parameter based on the inverse of the reference value of that parameter;
- scaling the measured value of each parameter for the current sample using the scaling factor determined for that parameter whereby to produce a corresponding scaled measured value;
- displaying said scaled measured values for the current sample along said axes and joining said scaled measured values into a polygon.

BRIEF DESCRIPTION OF THE DRAWINGS

A method and apparatus embodying the invention will now be described, by way of non-limiting example, with reference to the accompanying diagrammatic drawings, in which.

BEST MODE OF CARRYING OUT THE INVENTION

Figure 1:
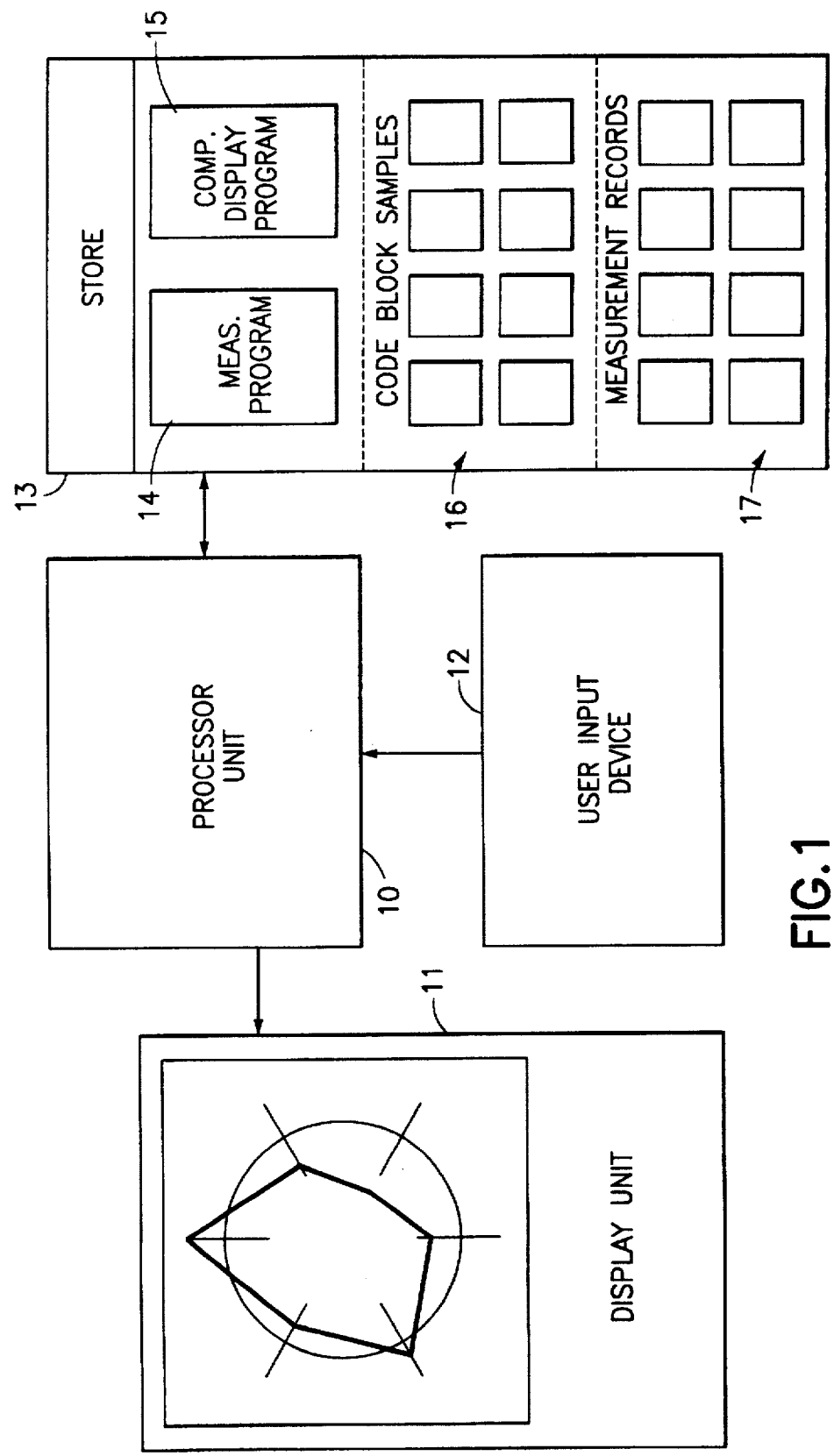
FIG. 1 is a diagram of a computer system adapted to implement the present invention.

FIG. 1 is a diagram of a computer adapted under program control to implement the present invention. The main elements of the computer are a processor unit 10, a display unit 11, a user input device 12, and a storage device 13 storing both programs 14, 15 and data 16, 17.

In the present example, the samples of interest are blocks of computer code which are to be measured according to a number of parameters. In particular, the following parameters of each code block are of interest:

Number of lines of code,

Number of comment lines in the code,

Number of branches in the code,

Number of loops in the code,

Number of floating point instructions in the code,

Number of procedure/function calls in the code.

As indicated at 16 in FIG. 1, each code block sample is, in the present case, stored in the storage device 13.

A measurement program 14 initiated by a user through the input device 12, is operative to measure the value of each of the aforesaid parameters for the stored code-block sample. The results of this measurement process are stored in measurement records 17 also held in storage device 13. Each measurement record comprises a code-block sample identifier and a measured value of each parameter for the identified sample.

Details of the measurement program 14 will not described herein as programs for measuring the aforesaid parameters are already known and the measurement program is not itself part of the present invention.

What is important is the availability to the computer of the rdeasured parameter values of the samples of interest. Thus whilst in the present example these values were derived by operation of the computer itself, in other cases the sample parameter values could be derived elsewhere and then entered into the computer by any suitable means, including user input. External input will be the only option in many cases where the nature of the samples of interest requires external measurement.

Figure 2:
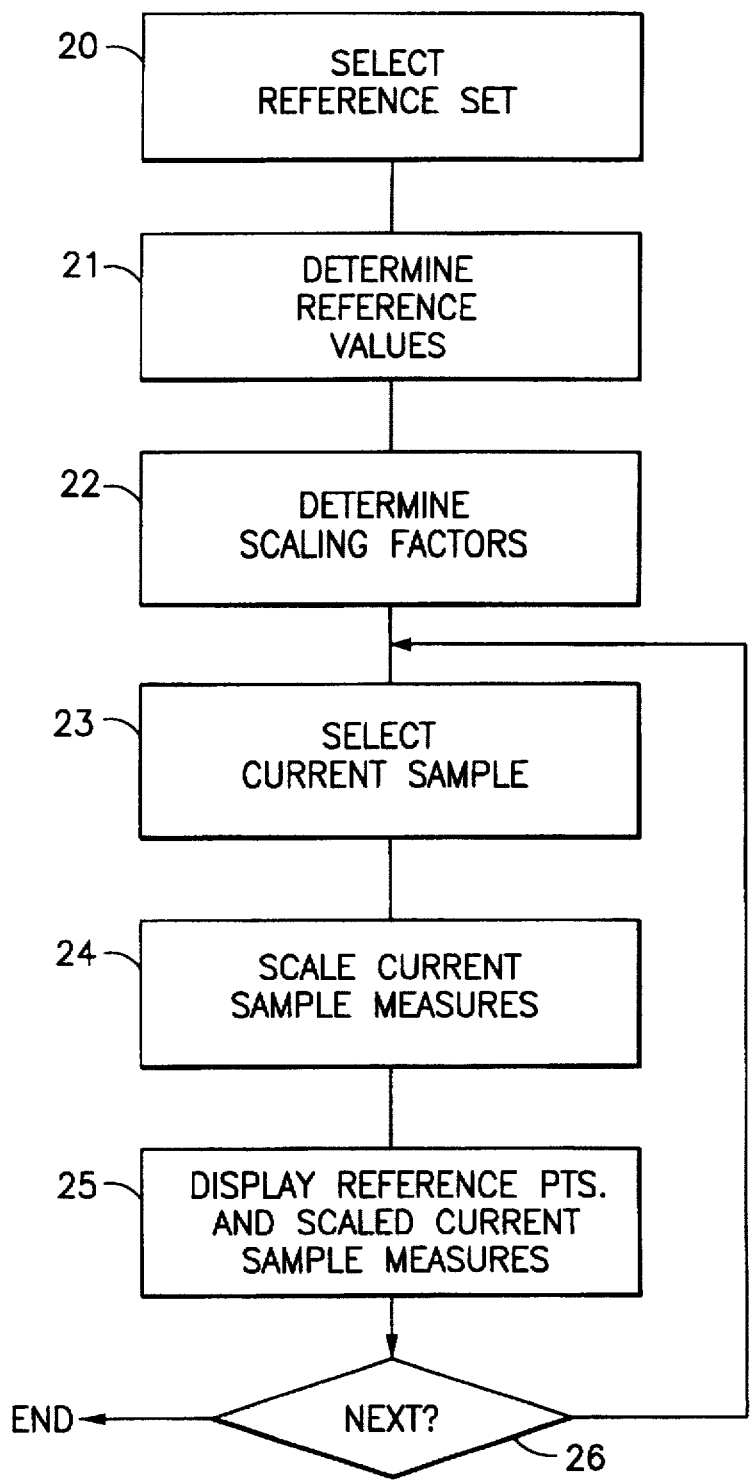
FIG. 2 is a flow chart of a comparison display program.

Once measurement records 17 have been derived for a group of samples of interest, the user can initiate operation of a comparative display program 15 which controls the computer to display spider diagrams in accordance with the present invention. The main steps of the comparative display program 15 will now be described with reference to FIG. 2.

According to the present invention, the or each sample that is of particular interest has its measured parameter values compared on a spider diagram with reference values derived from a reference set of one or more samples. The first step 20 of the comparative display program 15 involves the user defining the composition of the reference set of samples by selecting from amongst the group of samples whose measurement records 17 are available. This user selection may, for example, be done through displaying on display unit 11 a list of identifiers taken from the available measurement records 17.

In the current example where the samples are program code blocks (such as C or PASCAL functions or procedures), the reference set may comprise the set of code blocks relating to the same project or overall program.

Once the reference set has been specified, reference values for each measured parameter are determined in step 21 by using the measured parameter values of the sample or samples making up the reference set. Typically, though not essentially, the reference value of each parameter will be a mean of the measured values of that parameter for all samples in the reference set.

As will be described hereinafter, the reference value of each parameter is represented in the final spider diagram display by a predetermined reference value. This predetermined reference value will generally be the same for all parameters (for example, of unit value), but this is not necessarily so. Whatever value is used as the predetermined reference value for a parameter, there effectively exists a scaling factor between the reference value derived for that parameter in step 21 and the corresponding predetermined reference value; for example if the derived reference value is '87' and the predetermined reference value is '1', then the scaling factor between the two is 1/87. In step 22 of the comparative display program, the scaling factor associated with each parameter is determined and stored.

In step 23, the sample to be compared with the reference set is selected. This selection will generally involve user selection of the sample either from the group of samples for which measurement records are stored or from the subset of that group constituted by the samples or samples making up the aforesaid reference set of samples.

Once the particular current sample of interest has been selected, the scaling factors determined in step 22 are applied to the corresponding measured parameter values for that sample (step 24) to produce scaled current sample measures. Then in step 25, both the aforesaid predetermined reference values of the parameters and the scaled current-sample measures are displayed on a spider diagram.

Figure 3:
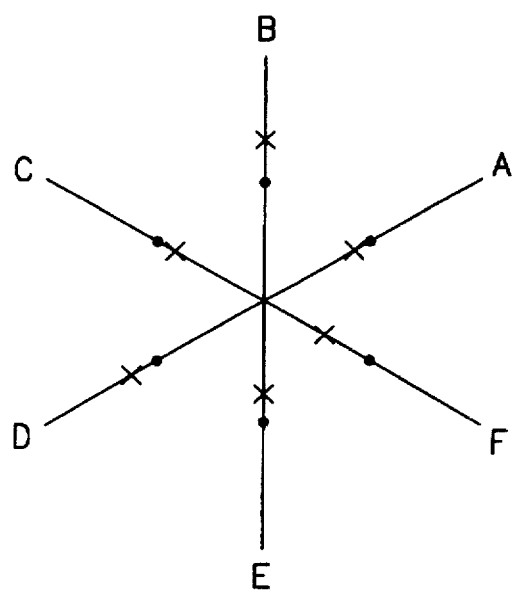
FIG. 3 illustrates a first form of spider diagram display.

FIG. 3 shows a simple form of spider diagram in which there are six equi-spaced radial axes A, B, C, D, E, F each used to represent values of a respective one of the measured sample parameters. For example, values of the "number of code lines" parameter may be displayed along axis A.

All axes have the same calibration so that if, as in the present case, the predetermined reference values of the parameters are the same, then these values when plotted along their corresponding axes will delimit a circle of radius equal to the common predetermined reference value. In FIG. 3, these predetermined reference values are shown as "*".

The scaled current-sample measures are also plotted along the corresponding axes, each value being depicted in FIG. 3 by "X".

Figure 4:
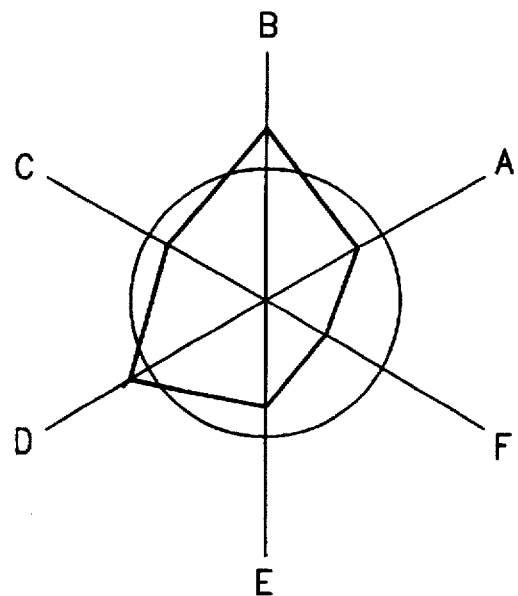
FIG. 4 illustrates a second form of spider diagram display.

The FIG. 3 spider diagram does not give an easily assimulated depiction of the displayed results. Matters are greatly improved by joining the plotted predetermined reference values by a circle (hereinafter, the 'reference circle'), and by joining the plotted scaled current-sample values to form a polygon. Such a display is shown in FIG. 4. Note that now the plotted values are not given any special emphasis (nor, indeed, are they separately plotted from the forms they define), the predetermined reference values being at the points of intersection of the reference circle with the axes A to F and the scaled current-sample values being at the vertices of the polygon they define.

The FIG. 4 display readily enables a user to see which parameters of the current sample of interest are above their corresponding references and which are below. Step 25 of the FIG. 2 program therefore preferably generates a display of the FIG. 4 form rather than that of the FIG. 3 form.

Figure 5:
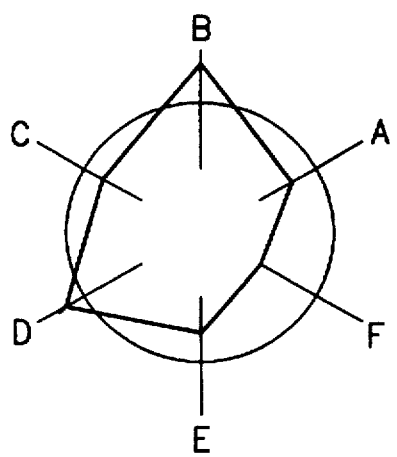
FIG. 5 illustrates a third form of spider diagram display.

FIG. 5 show a further form of spider display that may be generated in step 25. In this case, the axes A to F have been partially removed, each axis line only being left over the range between the maximum and minimum values for the parameters found in the reference set (these values having been scaled by the parameter scaling factor before being used to delimit the displayed portion of the corresponding axis). The determination of the maximum and minimum values of each parameter may take place, for example, in step 21 and the scaling of these values may take place in step 24.

In FIG. 5 the parameter plotted along axis B is at the maximum of the values found in the reference set, whilst the parameter plotted along axis F is at the minimum of the reference-set values. This is particularly meaningful where the sample of interest is a member of the reference set as it indicates that for the axis-B parameter, the current sample has the maximum value of the set, whilst for the axis-F parameter, the current sample has the minimum value of the set.

The FIG. 5 form of display is the preferred form.

Figure 6:
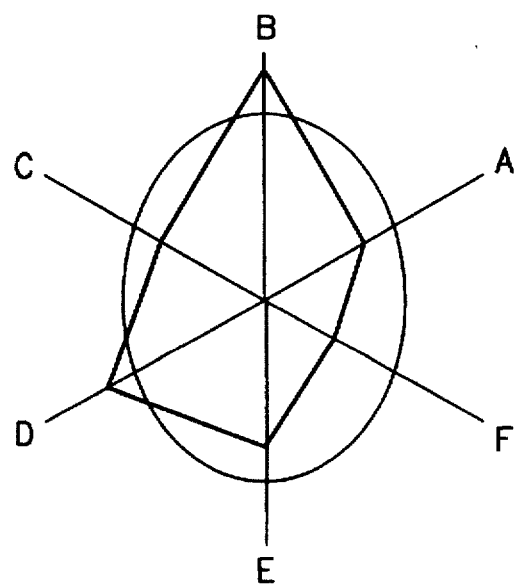
FIG. 6 illustrates a fourth form of spider diagram display.

The display shown in FIG. 6 is similar to that shown in FIG. 4 but in this case the predetermined reference values associated with axes B and E has been chosen to be larger than the predetermined reference values for the other axes. It is therefore no longer possible to generate a reference circle but instead a reference ellipse is displayed, intersecting all axes at the corresponding predetermined reference values. Such a form of display could be useful where it is wanted to emphasize certain parameters. Other reference shapes are also possible, preferably of smooth convex form.

Following the display of results for the current sample of interest the user may decide to select another sample for study or terminate the program (step 26).

Rather than having to specifically select samples of interest, where a user wishes to study all samples in turn from the reference set, then step 23 could be implemented as a mechanism to step through the reference set taking each constituent sample in turn as the sample currently of interest.

The above-described selection and scaling steps enables a user to readily select a reference set relevant to the sample which he/she wishes to study and then to scale the parameters values of that sample in accordance with a readily-comparable reference form (circle, ellipse, etc).

It will be appreciated that many variants are possible to the form of the invention particularly described above by way of example. Thus, the number of parameters measured and displayed can be different from six. Furthermore, generally more parameters will be measured than will be displayed at any one time, the user selecting which parameters are to be displayed. Provision may also be made for the user to adjust the predetermined reference value of each parameter.

We claim:

1. Apparatus for comparing measured values of a plurality of parameters of a current sample of interest with reference values for said parameters, said apparatus comprising:

a data store for storing measurements of said parameters for each sample of a group of samples;

selection means enabling user selection, from said group of samples, of a reference set of at least one sample;

processing means comprising:

first means for processing said measurements related to the reference set to derive therefrom respective reference values for said parameters for said reference set;

second means for determining for each said parameter a respective scaling factor corresponding to that adapted to transform the reference value for that parameter into a predetermined reference-point value, and third means for taking the said measured value of each parameter of said current sample, and applying thereto the scaling factor determined for that parameter whereby to produce a corresponding scaled measured value; and display means for displaying for each parameter along a respective one of a plurality of axes, the predetermined reference-point value and the scaled measured value determined for that parameter, said plurality of axes extending radially from a common point in angularly spaced relation.

2. Apparatus according to claim 1, wherein said reference set comprises a plurality of samples including said current sample.

3. Apparatus according to claim 2, further comprising means enabling user selection of any desired one of said samples of said reference set as said current sample.

4. Apparatus according to claim 2, further comprising means for stepping through said set to take each sample in turn as said current sample.

5. Apparatus according to claim 1, wherein where said reference set is composed of a plurality of samples, said first means of the processing means is operative to derive the reference value of each parameter as a mean of the measurements for that parameter associated with the samples in said reference set.

6. Apparatus according to claim 1, wherein said processing means further comprises means for determining for each said parameter, in the case where said reference set is composed of a plurality of samples, the corresponding maximum and minimum measurements for the samples in said reference set, said display mean displaying said maximum and minimum values along the corresponding axis.

7. Apparatus according to claim 6, wherein said axes are not displayed by said display mean except between said maximum and minimum values.

8. Apparatus according to claim 1, wherein the displayed said reference-point values together delimit a smooth convex form.

9. Apparatus according to claim 8, wherein the display means includes means for displaying a reference pattern corresponding to said smooth convex form.

10. Apparatus according to claim 1, wherein said display means includes means for displaying a polygon joining the displayed scaled measured values.

11. Apparatus according to claim 1, wherein said display means displays only a portion of each of said axes.

12. A method of comparing measured values of a plurality of parameters of a current sample of interest with reference values for said parameters, said method comprising the steps of:

providing measurements of said parameters for each sample of a group of samples;

selecting from said group a reference set of a plurality of said samples;

processing said measurements to derive for each parameter a reference value corresponding to a mean of the measurements for that parameters for the samples in said reference set;

providing a display including a reference circle of unit radius from the centre of which extend, at least notionally, a plurality of angularly spaced axes, each said axis corresponding to a said parameter and the intersection of that axis with the reference circle defining a reference point representing said reference value for that parameter;

determining a scaling factor for each parameter based on the inverse of the reference value of that parameter;

scaling the measured value of each parameter for the current sample using the scaling factor determined for that parameter whereby to produce a corresponding scaled measured value;

displaying said scaled measured values for the current sample along said axes and joining said scaled measured values into a polygon.

13. A method according to claim 12, further comprising the steps of determining for each parameter the corresponding maximum and minimum measurements for the samples in said reference set, and displaying said maximum and minimum values along the corresponding axis; said axes only being displayed between said maximum and minimum values.

* * * * *